United States Patent
Han et al.

(10) Patent No.: US 11,389,107 B2
(45) Date of Patent: Jul. 19, 2022

(54) APPARATUS AND METHOD FOR EVALUATING SKIN TIGHTENING

(71) Applicant: AMOREPACIFIC CORPORATION, Seoul (KR)

(72) Inventors: Ji Yeon Han, Yongin-si (KR); Eun Joo Kim, Yongin-si (KR); Hae Kwang Lee, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 995 days.

(21) Appl. No.: 16/080,543

(22) PCT Filed: Feb. 24, 2017

(86) PCT No.: PCT/KR2017/002050
§ 371 (c)(1),
(2) Date: Aug. 28, 2018

(87) PCT Pub. No.: WO2017/150846
PCT Pub. Date: Sep. 8, 2017

(65) Prior Publication Data
US 2021/0186412 A1      Jun. 24, 2021

(30) Foreign Application Priority Data
Feb. 29, 2016   (KR) .................. 10-2016-0023858

(51) Int. Cl.
*A61B 5/00* (2006.01)
*A61B 5/107* (2006.01)

(52) U.S. Cl.
CPC ............ *A61B 5/442* (2013.01); *A61B 5/0055* (2013.01); *A61B 5/0059* (2013.01); *A61B 5/107* (2013.01); *A61B 2562/0238* (2013.01)

(58) Field of Classification Search
CPC ..... A61B 5/442; A61B 5/0055; A61B 5/0059; A61B 5/107; A61B 2562/0238; A61B 5/00
(Continued)

(56) References Cited

U.S. PATENT DOCUMENTS 8,175,689 B2 * 5/2012 Hunter-Jones ....... A61B 5/4875
                                                       600/476
2004/0202685 A1   10/2004 Manzo
(Continued)

FOREIGN PATENT DOCUMENTS

CN          1535677       10/2004
CN          103876709      6/2014
(Continued)

OTHER PUBLICATIONS

Chung-Yi Chiang, et al., "Mechanical Characterization of Cosmetic and Viscoelastic Effects of Firming Polymers", American Chemical Society/Oxford University Press, (Jan. 1, 2013), vol. 1148, pp. 175-189.
(Continued)

*Primary Examiner* — May A Abouelela
(74) *Attorney, Agent, or Firm* — Cantor Colburn LLP

(57) ABSTRACT

Embodiments relate to an apparatus for evaluating skin tightening and a method for evaluating skin tightening by using the same, the apparatus comprising: a suction device for suctioning skin by a predetermined pressure for a predetermined time; a height measurement unit for measuring the height of the skin, which is changed by the suctioning; and a skin tightening evaluation unit for evaluating the degree of skin tightening on the basis of the measured height.

9 Claims, 3 Drawing Sheets

(58) Field of Classification Search
USPC .................................................. 600/306
See application file for complete search history.

(56) References Cited

U.S. PATENT DOCUMENTS

| | | | |
|---|---|---|---|
| 2004/0266656 A1 | 12/2004 | Sakurai | |
| 2008/0087098 A1 | 4/2008 | Qu et al. | |
| 2008/0221406 A1* | 9/2008 | Baker | A61B 5/0075 600/306 |
| 2010/0286493 A1* | 11/2010 | Duncan | A61B 5/0053 600/306 |
| 2013/0245454 A1* | 9/2013 | Taskinen | A61B 5/03 600/473 |
| 2014/0081095 A1* | 3/2014 | Krishnan | A61B 5/0059 600/306 |
| 2014/0276232 A1 | 9/2014 | Ruff | |
| 2015/0173996 A1* | 6/2015 | Grez | A61B 5/0057 600/587 |
| 2017/0119290 A1* | 5/2017 | Cai | A61B 5/0055 |
| 2017/0347939 A1* | 12/2017 | Tang | A61B 5/442 |

FOREIGN PATENT DOCUMENTS

| | | |
|---|---|---|
| CN | 104799857 | 7/2015 |
| JP | 06098862 A | 4/1994 |
| JP | H698862 | 4/1994 |
| JP | 2656650 B2 | 9/1997 |
| JP | 11137525 | 5/1999 |
| JP | 2004160020 | 6/2004 |
| JP | 2009045473 | 3/2009 |
| JP | 2012161371 | 8/2012 |
| JP | 2014121605 A | 7/2014 |
| KR | 200337911 Y1 | 1/2004 |
| KR | 1020100119314 | 11/2010 |
| KR | 1020120059122 | 6/2012 |
| KR | 101506978 B1 | 4/2015 |
| WO | 2008003146 | 1/2008 |

OTHER PUBLICATIONS

Erika Sandford, "Capturing Skin Properties from Dynamic Mechanical Analyses", Massachusetts Institute of Technology, (Jun. 28, 2012), pp. 1-84.
Extended European Search Report—European Application No. 17760250.5 dated Aug. 28, 2019, citing references listed within.
Chinese Office Action—Chinese Application No. 201780026371.9 dated Sep. 25, 2020, citing references listed within.
International Search Report and Written Opinion for application No. PCT/KR2017/002050 dated May 31, 2017, citing the above reference(s).
Decision of Refusal—Japanese Patent Application No. 2018-545346 dated May 6, 2021, citing references listed within.
Second Office Action—Chinese Application No. 201780026371.9 dated Apr. 15, 2021, citing references listed within.
Korean Office Action—Korean Application No. 10-2016-0023858 dated Nov. 30, 2021, citing references listed within.

* cited by examiner

[FIG. 1]
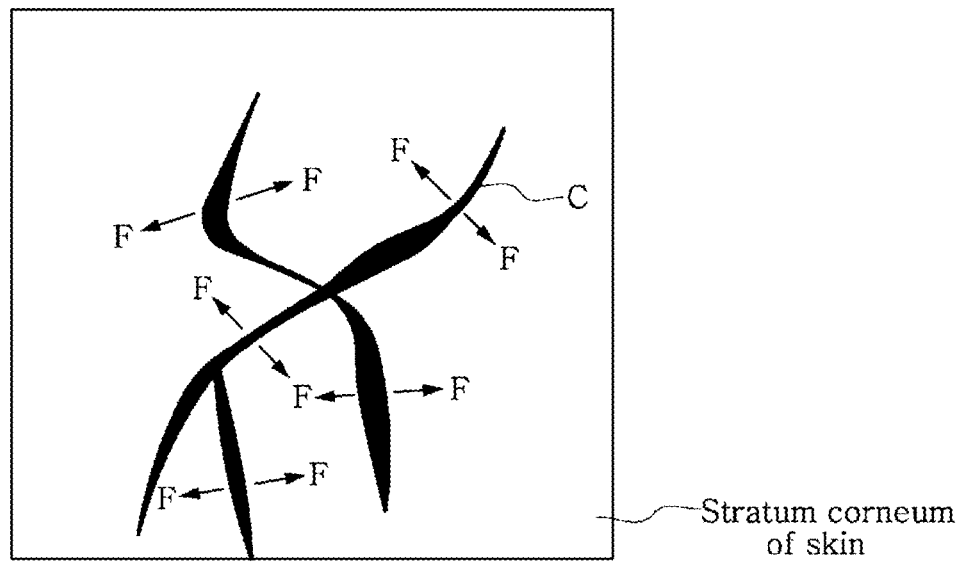
[FIG. 2]
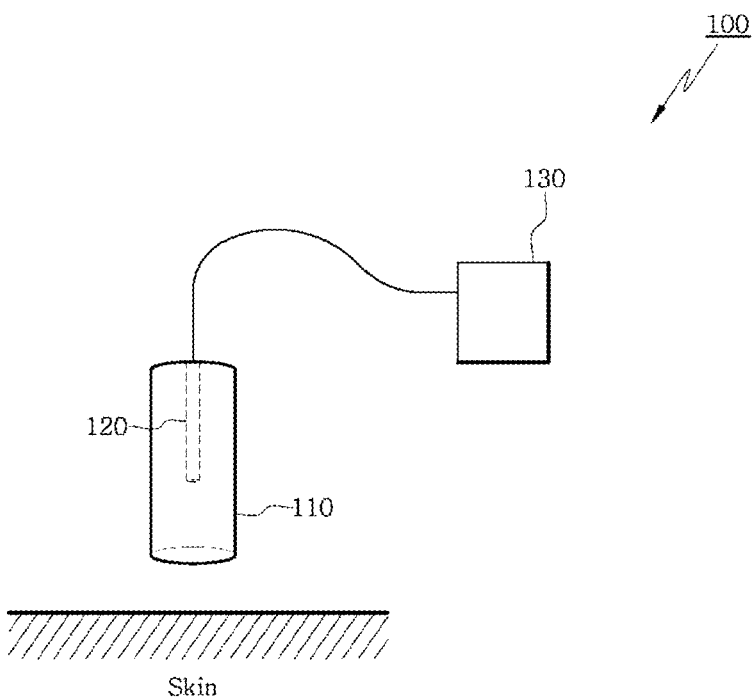

[FIG. 3]
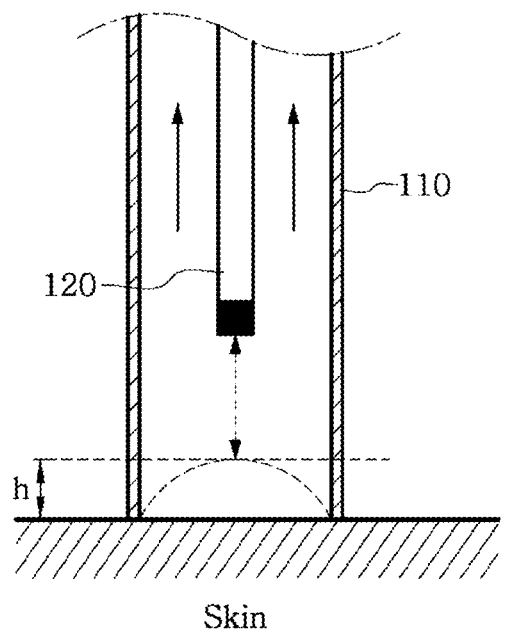
Skin
[FIG. 4]
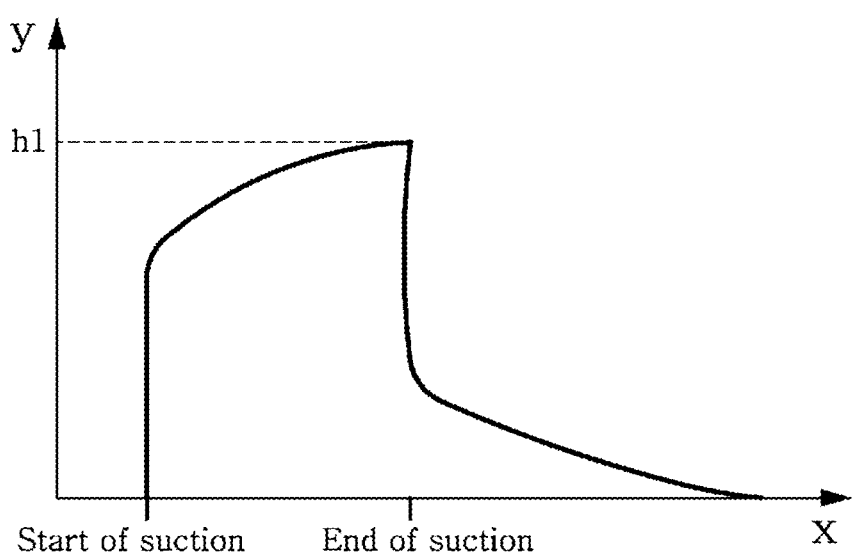

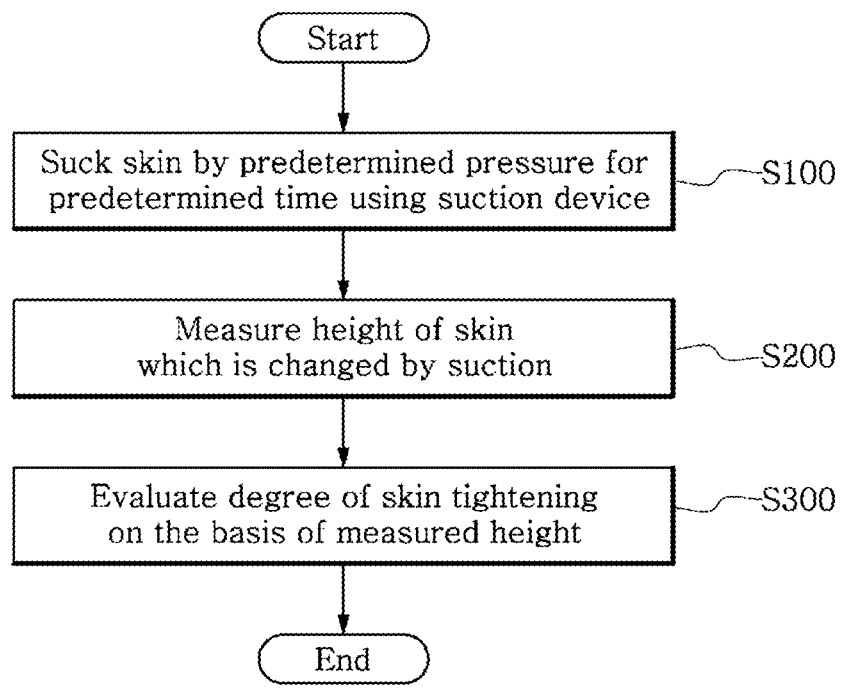
[FIG. 5]

APPARATUS AND METHOD FOR EVALUATING SKIN TIGHTENING

TECHNICAL FIELD

The present disclosure relates to an apparatus and method for evaluating skin tightening. More particularly, the present disclosure relates to an apparatus and method for evaluating the degree of skin tightening on the basis of the height of the skin raised by suction of the skin for a predetermined time by a predetermined pressure.

BACKGROUND ART

Conventionally, criteria and methods for evaluating various properties of the skin are presented. For example, skin elasticity is evaluated by sucking the skin periodically a few times using a skin suction device (e.g., Courage & Khazaka electronic GmbH, Cutometer MPA 580), and separately measuring each of overall elasticity, net elasticity and biological elasticity of the skin on the basis of the results. The skin elasticity is relevant to the recovery ability to restore to the original location when the skin is subjected to the external force, and it is completely different from skin tightening or tension.

There have been apparatuses for measuring skin elasticity as well as moisture content of skin and skin texture, but there is no apparatus for measuring and evaluating skin tightening.

RELATED LITERATURES

Patent Literatures (Patent Literature 1) US Patent Publication No. 2014-0276232 (2014.9.18)

DISCLOSURE

Technical Problem

To solve the above-described problem, there is a demand for an apparatus and method for defining skin tightening and measuring and evaluating the degree of skin tightening.

Technical Solution

An apparatus for evaluating skin tightening according to an embodiment of the present disclosure includes a suction device for sucking skin by a predetermined pressure for a predetermined time, a height measurement unit for measuring the height of the skin which is changed by the suction, and a skin tightening evaluation unit for evaluating the degree of skin tightening on the basis of the measured height.

In a preferred embodiment, the suction device may suck the skin once.

In a preferred embodiment, the predetermined pressure may be 50 mmbar to 350 mmbar.

In a preferred embodiment, the predetermined time may be 0.5 sec to 1.5 sec.

In a preferred embodiment, the skin suction by the suction device may be performed after 10 min or less have elapsed since a user washed a face.

In a preferred embodiment, the skin tightening evaluation unit may evaluate the degree of skin tightening on the basis of a maximum height of the measured height.

In a preferred embodiment, the skin tightening evaluation unit may evaluate the degree of tightening as being lower with the increasing maximum height.

In a preferred embodiment, the suction device may include a cylindrical body and a fan to suck air in the body.

In a preferred embodiment, the height measurement unit may output infrared light to the skin, and measure the height of the skin by analyzing the reflected infrared light.

A method for evaluating skin tightening according to an embodiment of the present disclosure includes sucking skin by a predetermined pressure for a predetermined time using a suction device, measuring the height of the skin which is changed by the suction, and evaluating the degree of skin tightening on the basis of the measured height.

In a preferred embodiment, the sucking the skin may be performed once by a predetermined pressure for a predetermined time.

In a preferred embodiment, the predetermined pressure may be 50 mmbar to 350 mmbar.

In a preferred embodiment, the predetermined time may be 0.5 sec to 1.5 sec.

In a preferred embodiment, the sucking the skin may be performed after 3 min to 10 min have elapsed since a user washed a face.

In a preferred embodiment, the evaluating the degree of skin tightening may include evaluating the degree of skin tightening on the basis of a maximum height of the measured height, wherein the degree of tightening is evaluated as being lower with the increasing maximum height.

A program stored in a computer-readable storage medium according to an embodiment of the present disclosure may include instructions for performing the above-described method for evaluating skin tightening.

Advantageous Effects

According to an embodiment of the present disclosure, it is possible to quantify the degree of skin tightening. As a result, there is an advantage that the performance of products for diminishing skin tightening can be quantitatively determined.

Additionally, according to an embodiment of the present disclosure, using the existing suction and skin height equipment, a user's skin tightening can be measured. For example, equipment such as Courage & Khazaka electronic GmbH's Cutometer MPA 580 may be used.

Additionally, according to an embodiment of the present disclosure, it is possible to measure skin tightening using a height measurement sensor and a suction device that apply a predetermined pressure, contributing to the size reduction of equipment.

DESCRIPTION OF DRAWINGS

FIG. 1 is a conceptual diagram of skin illustrating skin tightening.

FIG. 2 is a configuration diagram of an apparatus for evaluating skin tightening according to an embodiment of the present disclosure, and FIG. 3 is a diagram schematically showing a suction device 110 and a height measurement unit 120 according to an embodiment of the present disclosure.

FIG. 4 is a graph showing the results of measuring, by a height measurement unit, the height of the skin which is changed by suction.

FIG. 5 is a flowchart of a method for evaluating skin tightening according to an embodiment of the present disclosure.

BEST MODE

The terminology used herein is for the purpose of describing particular embodiments only and is not intended to be limiting of this disclosure. As used herein, the singular forms are intended to include the plural forms as well, unless the context clearly indicates otherwise. It should be understood that the term "comprising" or "including" when used in this specification, specifies the presence of stated features, integers, steps, operations, elements, components or groups thereof, but does not preclude the presence or addition of one or more other features, integers, steps, operations, elements, components or groups thereof.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein. In the drawings, like reference numerals denote like elements. However, in describing the embodiments, when it is determined that a certain detailed description of relevant known functions or components may unnecessarily render the essential subject matter of the present disclosure vague, its detailed description is omitted herein. Additionally, the size of each element in the drawings may be exaggerated for clarity, and does not represent the actual size.

The embodiments described herein may have aspects of entirely hardware, partly hardware and partly software, or entirely software. The "unit", "module", "device" or "system" as used herein refers to a computer-related entity, either hardware, a combination of hardware and software, or software. For example, the unit, module, device or system as used herein may be a process in execution, a processor, an object, an executable, a thread of execution, a program and/or a computer, but is not limited thereto. For example, both the application running on the computer and the computer may correspond to the unit, module, device or system as used herein.

The embodiments have been described with reference to the flowchart presented in the drawings. For simplicity of description, the method has been shown and described as a series of blocks, but the present disclosure is not limited to the sequence of the blocks, and some of the blocks may be performed in a different sequence from those shown and described herein or concurrently with the other blocks, and it is possible to implement a variety of other branches, flow paths and sequences of blocks that achieve identical or similar results. Additionally, all the blocks shown to implement the method described herein may not be required. Further, the method according to an embodiment of the present disclosure may be implemented in the form of a computer program for performing a series of steps, and the computer program may be recorded on a computer-readable recording medium.

The present disclosure defines skin tightening and can quantitatively evaluate the degree of tightening. FIG. 1 is a conceptual diagram of skin illustrating skin tightening. Referring to FIG. 1, after washing, the stratum corneum of skin is rapidly dehydrated. Due to dehydration, the moisture content in stratum corneum of skin is lower than before washing. Due to the reduced moisture content, microcrack C occurs in the stratum corneum of skin, and the skin feels taut around the crack C by tension F and a user's skin feels tight. Meanwhile, due to the reduced amount of moisture, the skin tension increases. This phenomenon and the user's feeling are defined as skin tightening.

The present disclosure sucks the skin, and evaluates the degree of skin tightening on the basis of the height of the skin raised by suction. Although the embodiments of the present disclosure set the suction intensity, time and number as described below based on data obtained by experiments and questionnaire, the present disclosure is not limited thereto.

Hereinafter, the embodiments of the present disclosure will be described in detail with reference to the accompanying drawings.

FIG. 2 is a configuration diagram of an apparatus for evaluating skin tightening according to an embodiment of the present disclosure, and FIG. 3 is a diagram schematically showing a suction device 110 and a height measurement unit 120 according to an embodiment of the present disclosure.

Referring to FIG. 2, the apparatus 100 for evaluating skin tightening includes the suction device 110, the height measurement unit 120, and a skin tightening evaluation unit 130.

The suction device 110 sucks the skin by a predetermined pressure for a predetermined time. The suction device 110 may include a cylindrical body and a fan that can suck air in the body. However, this configuration of the suction device is provided for illustration only, and the suction device used in the present disclosure may include any type of device that can pull the skin up by a predetermined pressure for a predetermined time.

In an embodiment, the suction device 110 may suck the skin at least once. However, skin suction for evaluation of tightening is preferably performed once. In general, to evaluate elasticity of the skin, skin suction is periodically repeated and the repeated results are used. However, skin suction more than once may cause the tiring effect according to the properties of the skin, and skin crack that is one factor of tightening is damaged, making it difficult to accurately measure skin tightening. Accordingly, skin suction by the suction device is preferably performed once.

Additionally, according to an embodiment, the pressure (i.e., pressure in the cylindrical body) at which the suction device sucks the skin is preferably 50 mmbar to 350 mmbar, and the time during which the suction device sucks the skin is preferably 0.5 sec to 1.5 sec. The above pressure and time are ranges determined by experimentation, and when sucking the skin and measuring skin height changes in the above range, skin tightening evaluation information that is best suited to the user's feeling can be acquired.

Additionally, in an embodiment, skin suction by the suction device 110 may be performed after 3 min to 10 min have elapsed since the user washed the face, but the present disclosure is not limited thereto.

The height measurement unit 120 may measure the height of the skin which is changed by suction. Referring to FIG. 3, it is found that the skin is raised as much as a height h by the suction device 110. The height measurement unit 120 may measure skin height changes before suction and from the start of suction to the end of suction. The time from the start of suction to the end of suction is preferably 0.5 sec to 1.5 sec as described above.

FIG. 4 is a graph showing the results of measuring, by the height measurement unit, the height of the skin which is changed by suction. Referring to FIG. 4, the skin height sharply increases after the start of suction, and then gradually increases and reaches the maximum point h1.

As shown in FIG. 3, the height measurement unit 120 may be positioned inside the suction device 110, but the present disclosure is not limited thereto. Additionally, the height measurement unit 120 may use infrared light to measure the skin height changes, but the present disclosure is not limited thereto.

The skin tightening evaluation unit 130 evaluates the degree of skin tightening on the basis of the measured height. The skin tightening evaluation unit 130 evaluates the degree of skin tightening on the basis of a maximum height (h1 in FIG. 3) of the measured height. Additionally, the skin tightening evaluation unit 130 may evaluate the degree of tightening as being lower with the increasing maximum height of the raised skin.

For example, when the maximum height value of the skin measured after using cleanser A is 1 and the maximum height value of the skin measured after using cleanser B is 1.1, the skin tightening evaluation unit 130 may evaluate that the degree of skin tightening after using cleanser A is larger (severer).

The skin tightening evaluation unit 130 may classify the degree of tightening according to the range of maximum height values of the skin raised by suction. For example, when the maximum height value of the skin raised by suction is 1-1.1, the degree of tightening may be 10, and when the maximum height value of the skin is 1.1-1.2, the degree of tightening may be 9. The values mentioned herein are for illustration only.

Referring to FIG. 5, the method for evaluating skin tightening includes sucking the skin by a predetermined pressure for a predetermined time using the suction device (S100), measuring the height of the skin which is changed by suction (S200), and evaluating the degree of skin tightening on the basis of the measured height (S300).

The step (S100) of sucking the skin may be performed once by a predetermined pressure for a predetermined time. Here, the predetermined pressure may be 50 mmbar to 350 mmbar, and the predetermined time may be 0.5 sec to 1.5 sec, but the present disclosure is not limited thereto. Additionally, the step (S100) of sucking the skin may be performed after 10 min or less have elapsed since the user washed the face. Preferably, the suction step (S100) may be performed after the elapse of 3 min to 10 min, but the present disclosure is not limited thereto.

The step (S300) of evaluating the degree of skin tightening may include evaluating the degree of skin tightening on the basis of a maximum height of the measured height, wherein the degree of tightening is evaluated as being lower with the increasing maximum height.

The program according to an embodiment of the present disclosure includes instructions for performing the method for evaluating skin tightening as described above, and may be stored in a computer-readable storage medium.

The computer-readable storage medium according to an embodiment of the present disclosure may store the instructions for performing the method for evaluating skin tightening as described above.

The present disclosure has been hereinabove described with reference to the embodiments shown in the accompanying drawings, but this is for illustration only and those having ordinary skill in the art will appreciate that various modifications and variations may be made thereto. However, it should be noted that such modifications fall in the scope of technical protection of the present disclosure. Therefore, the true scope of technical protection of the present disclosure should be defined by the technical spirit of the appended claims.

INDUSTRIAL APPLICABILITY

According to an embodiment of the present disclosure, it is possible to quantify the degree of skin tightening. As a result, there is an advantage that the performance of products for diminishing skin tightening can be quantitatively determined. Additionally, according to an embodiment of the present disclosure, using the existing suction and skin height equipment, a user's skin tightening can be measured. For example, equipment such as Courage & Khazaka electronic GmbH's Cutometer MPA 580 may be used. Additionally, according to an embodiment of the present disclosure, it is possible to measure skin tightening using a height measure sensor and a suction device that apply a predetermined pressure, contributing to the size reduction of equipment.

The invention claimed is:

1. An apparatus for evaluating skin tightening, comprising:
   a suction device configured to suck a skin being washed using a cleanser by a predetermined pressure for a predetermined time;
   a height measurement part configured to measure a height of the skin, which is changed by the suction; and
   a skin tightening evaluation part configured to evaluate a degree of skin tightening based on the measured height to evaluate a performance of the cleanser for diminishing skin tightening that is caused by cracks in a stratum corneum of skin due to reduction of moisture content after washing,
   wherein the predetermined pressure has 50 mmbar to 350 mmbar, and the predetermined time is 0.5 second to 1.5 second,
   wherein the skin tightening evaluating part is configured to evaluate the degree of skin tightening based on a maximum height of the measured height during the predetermined time,
   wherein the skin tightening evaluating part is configured to evaluate the degree of tightening as being lower with the increasing maximum height.

2. The apparatus for evaluating skin tightening according to claim 1, wherein the suction device is configured to suck the skin once.

3. The apparatus for evaluating skin tightening according to claim 1, wherein the skin suction by the suction device is performed after 10 min or less have elapsed since a user washed the skin of the user.

4. The apparatus for evaluating skin tightening according to claim 1, wherein the suction device includes a cylindrical body and a fan to suck air in the cylindrical body.

5. The apparatus for evaluating skin tightening according to claim 1, wherein the height measurement part is configured to output infrared light to the skin, and measures the height of the skin by analyzing the infrared light reflected from the skin.

6. A method for evaluating skin tightening, comprising:
   sucking a skin being washed using a cleanser by a predetermined pressure for a predetermined time by a suction device;
   measuring a height of the skin changed due to the suction; and
   evaluating a degree of the skin tightening based on the measured height to evaluate a performance of the cleanser for diminishing skin tightening that is caused by cracks in a stratum corneum of skin due to reduction of moisture content after washing,
   wherein the predetermined pressure has 50 mmbar to 350 mmbar, and the predetermined time is 0.5 second to 1.5 second, wherein the evaluating the degree of skin tightening is evaluating the degree of skin tightening on the basis of a maximum height of the measured height during the predetermined time,
wherein the degree of skin tightening is evaluated to be lower as the measured maximum height of the skin increases.

7. The method for evaluating skin tightening according to claim 6, wherein the sucking the skin is performed once by the predetermined pressure for the predetermined time.

8. The method for evaluating skin tightening according to claim 6, wherein the sucking the skin is performed after 10 min or less have elapsed since a user washed the skin of the user.

9. A program stored in a computer-readable storage medium, comprising instructions for performing the evaluation method according to claim 6.

* * * * *